US006506737B1

(12) United States Patent
Hei et al.

(10) Patent No.: US 6,506,737 B1
(45) Date of Patent: Jan. 14, 2003

(54) ANTIMICROBIAL PHOSPHONIUM AND SULFONIUM POLYHALIDE COMPOSITIONS

(75) Inventors: Robert D. P. Hei, Baldwin, WI (US); Kim Smith, Woodbury, MN (US)

(73) Assignee: Ecolab, Inc., St. Paul, MN (US)

( * ) Notice: Subject to any disclaimer, the term of this patent is extended or adjusted under 35 U.S.C. 154(b) by 0 days.

(21) Appl. No.: 09/542,087

(22) Filed: Apr. 5, 2000

(51) Int. Cl.$^7$ .................. A01N 57/00; A01N 57/18; A01N 57/20; A01N 57/22; A01N 57/24; A01N 59/00; A61L 2/16; A61L 2/18; A61L 2/23

(52) U.S. Cl. .................. 514/75; 514/79; 514/95; 514/99; 514/114; 514/120; 514/125; 514/126; 514/129; 514/134; 514/139; 514/372; 514/557; 514/558; 514/574; 514/714; 424/402; 424/405; 424/443; 424/600; 424/613; 424/614; 424/615; 424/616; 424/660; 424/661; 424/662; 424/663; 424/664; 424/665; 424/667; 424/668; 424/669; 424/712; 424/718; 424/723; 422/4; 422/5; 422/28; 422/29; 422/37; 210/753; 210/754; 210/755; 210/756; 210/758; 210/759; 210/760; 210/764

(58) Field of Search .................. 514/75, 134, 139, 514/79, 95, 99, 114, 120, 125, 126, 129, 372, 557–558, 574, 714; 424/402, 405, 443, 600, 613–616, 660–665, 667–669, 712, 718, 723; 422/4, 5, 28, 29, 37; 210/753–756, 758–760, 764

(56) References Cited

U.S. PATENT DOCUMENTS

| | | | |
|---|---|---|---|
| 3,374,256 A | 3/1968 | Driscoll et al. ............. 556/18 |
| 3,437,473 A | 4/1969 | Driscoll et al. ............. 504/165 |
| 3,642,989 A | * 2/1972 | Martin et al. | |
| 3,778,476 A | 12/1973 | Rembaum et al. ......... 525/539 |
| 3,898,336 A | 8/1975 | Rembaum et al. ......... 424/447 |
| 4,076,622 A | 2/1978 | Costin ....................... 424/419 |
| 4,187,183 A | 2/1980 | Hatch ........................ 210/501 |
| 4,190,529 A | 2/1980 | Hatch ........................ 210/668 |
| 4,661,518 A | 4/1987 | LaMarre et al. ........... 514/528 |
| 4,673,509 A | 6/1987 | Davis et al. ............... 210/699 |
| 4,775,407 A | 10/1988 | Talbot et al. ............... 504/207 |
| 4,800,235 A | 1/1989 | LaMarre et al. ........... 514/643 |
| 4,822,513 A | 4/1989 | Corby ....................... 510/234 |
| 4,861,511 A | 8/1989 | Kaplan ...................... 510/193 |
| 4,960,590 A | 10/1990 | Hollis et al. ............... 525/540 |
| 5,047,164 A | 9/1991 | Corby ....................... 510/383 |
| 5,093,078 A | 3/1992 | Hollis et al. ............... 422/16 |
| 5,139,561 A | 8/1992 | Talbot et al. ............... 504/153 |
| 5,202,047 A | 4/1993 | Corby ....................... 510/382 |
| 5,385,896 A | 1/1995 | Bryan et al. ............... 514/129 |
| 5,403,505 A | * 4/1995 | Hachmann et al. ........ 252/106 |
| 5,431,908 A | 7/1995 | Lund ......................... 424/78.1 |
| 5,606,105 A | 2/1997 | Davis et al. ............... 562/8 |
| 5,639,452 A | 6/1997 | Messier ..................... 424/78.1 |
| 5,658,467 A | 8/1997 | LaZonby et al. .......... 210/754 |
| 5,702,684 A | 12/1997 | McCoy et al .............. 424/10.3 |
| 5,741,757 A | 4/1998 | Cooper et al. ............. 504/153 |
| 5,922,745 A | 7/1999 | McCarthy et al. ......... 514/372 |
| 6,187,516 B1 * | 2/2001 | Loccufier et al. .......... 430/350 |
| 6,214,777 B1 * | 4/2001 | Li et al. .................... 508/388 |
| 6,300,044 B1 * | 10/2001 | Uytterhoeven et al. .... 430/350 |
| 6,310,013 B1 * | 10/2001 | Lokkesmoe et al. ....... 508/502 |
| 6,383,725 B2 * | 5/2002 | Loccufier et al. .......... 430/350 |

FOREIGN PATENT DOCUMENTS

| | | | |
|---|---|---|---|
| CA | 1269300 | | 5/1990 |
| DE | 2059379 A | | 6/1984 |
| EP | 0 156 646 A1 | | 10/1985 |
| EP | 0 799 570 A1 | | 10/1997 |
| EP | 0 821 268 | * | 1/1998 |
| JP | 8-40811 | * | 2/1996 |
| JP | 10-57472 | * | 3/1998 |
| JP | 10-273408 | * | 10/1998 |

OTHER PUBLICATIONS

Kanazawa, A., et al., "Polymeric Phosphonium Salts as a Novel Class of Cationic Biocides, VI. Antibacterial Activity of Fibers Surface–Treated with Phosphonium Salts Containing Trimethoxysilane Groups," Journal of Applied Polymer Science, vol. 52 (1994) 641–647.

Kanazawa, A., et al., "Polymeric Phosphonium Salts as a Novel Class of Cationic Biocides, III. Immobilization of Phosphonium Salts by Surface Photografting and Antibacterial Activity of the Surface–Treated Polymer Films," Journal of Polymer Science: Part A: Polymer Chemistry, vol. 31, No. 6, May 1993, 1467–1472.

Nurdin, N., et al., "Biocidal Polymers Active by Contact, III. Aging of Biocidal Polyurethane Coatings in Water," Journal of Applied Polymer Science, vol. 50 (1993) pp. 671–678.

Chemical Abstracts 124:310241c (1996).*
Chemical Abstracts 128:248639r ((1998).*
Chemical Abstracts 129:340815p (1998).*

* cited by examiner

Primary Examiner—John Pak
(74) Attorney, Agent, or Firm—Merchant & Gould P.C.

(57) ABSTRACT

An oxidizing species is described herein as a reaction product through an in situ preparation combining a protonizable phosphorus or sulfur compound, and a halide source at controlled proportions in an aqueous, non-aqueous, gel, aerosol, solid-phase or powdered media. The oxidizing species can be used to reduce microbial and viral populations on a surface or object or in a body or stream of water. The invention thus finds applications as a bleach, sanitizer, oxidant, or in any other application in which an oxidizing agent can be beneficially used alone or in a formulation.

59 Claims, No Drawings

ANTIMICROBIAL PHOSPHONIUM AND SULFONIUM POLYHALIDE COMPOSITIONS

FIELD OF THE INVENTION

The invention relates to antimicrobial compositions containing an oxidizing species. The materials are made by reacting cooperating ingredients at controlled proportions to form an antimicrobial that can have a variety of end uses. The antimicrobial species of the invention is generated in situ and is stable for limited periods, typically less than a few days.

BACKGROUND OF THE INVENTION

Peroxygen sanitizers and halogen sanitizers are known. Peroxygen sanitizers include compounds such as hydrogen peroxide, percarboxylic acids, percarbonates, perborates, etc. These materials are relatively well characterized and understood and are commonly used in a variety of end uses. Halogen sanitizers include compounds such as hypochlorite (HOCl), chlorine dioxide ($ClO_2$), perchlorate ($HClO_4$), perbromate ($HBrO_4$), and others. Halide and quaternary ammonium base sanitizers are also known. These materials are generally not considered oxidizing materials but provide sanitizing properties to materials.

One type of halogen based sanitizers are those that can contain species such as $I_3^{-1}$, $IBrCl^{-1}$, and other similar species. Representative examples of such materials include Rembaum et al., U.S. Pat. No. 3,898,336; Rembaum et al., U.S. Pat. No. 3,778,476; Hollis et al., U.S. Pat. No. 4,960,590; Hollis et al., U.S. Pat. No. 5,093,078 and Dammann, European Patent Application No. 156646. These references describe isolated polymeric quaternary ammonium polyhalides based on synthetic polymeric ionene (known in the industry as polymeric quats), epi-amine, and cationic acrylamide polymer resins (containing 2 or more cationic groups) precipitated with polyhalogens. Similarly, Corby, U.S. Pat. No. 4,822,513; Corby, U.S. Pat. No. 5,047,164; and Corby, U.S. Pat. No. 5,202,047 describe mixed interhalogen salts limited to 4 halogens with a maximum of one iodine or bromine atom per complex.

Asensio, EP 0 799 570 A1 discloses a five component antimicrobial mix containing two quaternary tri-iodides (prepared via conventional molecular halogen addition, not by in-situ reaction). LaZonby, et al., U.S. Pat. No. 5,658,467 describes the use of peracetic acid in combination with a non-oxidizing biocide for industrial process waters.

None of the aforementioned references teach the use of in-situ, labile antimicrobial compositions generated via halide salts and oxidants; especially peroxygen oxidants. All of these examples deal with stable, isolated antimicrobials that would remain in the application environment (e.g., food surface) indefinitely. In-situ, labile antimicrobial compositions utilizing quaternary or protonizable nitro en compounds complexed with polyhalides are described in U.S. Ser. No. 09/277,592 filed on Mar. 26, 1999, now U.S. Pat. No. 6,436,445 and Ser. No. 09/277,626 filed on Mar. 26, 1999 now abandoned.

Other compounds have been described in the art as having antimicrobial efficacy, including some compounds having phosphonium or sulfonium functionality. For example, nonsoluble, solid phase disinfectant resins that release halides include Costin, U.S. Pat. No. 4,076,622; Hatch, U.S. Pat. Nos. 4,187,183 and 4,190,529; Lund, U.S. Pat. No. 5,431,908; Messier, U.S. Pat. No. 5,639,452; and Bahr et al., DE 2 059 379.

Similar compounds are described in Nurdin et al., "Biocidal Polymers Active by Contact. III. Aging of Biocidal Polyurethane Coatings in Water," Journal of Applied Polymer Science, vol. 50 (1993) pp. 671–678; Kanazawa et al., "Polymeric Phosphonium Salts as a Novel Class of Cationic Biocides. III. Immobilization of Phosphonium Salts by Surface Photografting and Antibacterial Activity of the Surface-Treated Polymer Films," Journal of Applied Polymer Science: Part A: Polymer Chemistry, vol 31, No. 6 (1993) pp. 1467–1472; and Kanazawa et al., "Polymeric Phosphonium Salts as a Novel Class of Cationic Biocides. VI. Antibacterial Activity of Fibers Surface-Treated with Phosphonium Salts Containing Trimethoxysilane Groups," Journal of Applied Polymer Science, vol. 52 (1994) pp. 641–647.

Non-polymeric phosphonium compounds such as phosphonium sulfates and mono halides are also known as co-antimicrobials used in conjunction with other antimicrobial agents. Examples include LaMarre et al., U.S. Pat. Nos. 4,661,518 and 4,800,235 and Canadian Patent No. CA 1 269 300; Kaplan, U.S. Pat. No. 4,861,511; McCoy et al., U.S. Pat. No. 5,702,684; and McCarthy et al., U.S. Pat. No. 5,922,745.

Phosphorane trihalides are described as antimicrobials in Driscoll et al., U.S. Pat. Nos. 3,374,256 and 3,437,473. These patents disclose phosphonium polyhalides having C=P olefinic structures. A phosphonium biocide currently on the market is represented as $[(HOCH_2O)_4P]_2=SO_4^{2-}$, described for example in Davis et al., U.S. Pat. No. 4,673,509; Talbot et al., U.S. Pat. Nos. 4,775,407 and 5,139,561; Bryan et al., U.S. Pat. No. 5,385,896; Davis et al., U.S. Pat. No. 5,606,105; and Cooper et al., U.S. Pat. No. 5,741,757.

SUMMARY OF THE INVENTION

We have discovered a synergistic effect resulting from the combination of a source of protonizable phosphorous or sulfur, and a halide source, for example, an elemental halogen(s), or metal or ammonium halide salt(s), preferably including an iodide salt. More specifically, we have found that a synergistic oxidizing species is created from this combination. Since reaction is almost immediate, an in-situ aqueous or non-aqueous use solution can be available for use immediately after mixing as an antimicrobial or antiviral composition; or the active composition can be stabilized and post-incorporated into a nonaqueous liquid, gel, aerosol, powder, or solid formulation. It is also possible to produce solid sanitizing substrates containing this oxidizing species that have residual antimicrobial and antiviral effectiveness; such as in air filters or as packaging or plastic or as cutting board additives.

Accordingly, the invention is found in a composition for antimicrobial or antiviral use, the composition being the product of an in-situ reaction of a source of a protonizable phosphorus or sulfur compound, and a halide source.

The invention also resides in an antimicrobial or antiviral composition that includes a combination of a source of a protonizable phosphorus or sulfur compound, and a halide source, with the balance being water.

The invention is also found in a two-part liquid concentrate antimicrobial and antiviral composition. The first part includes about 0.1 to 80 wt-% of a source of a protonizable phosphorus or sulfur compound, with the balance being water. The second part includes about 0.1 to 80 wt-% of a halide source, with the balance being water.

Another embodiment of the invention is found in a method of reducing microbial or viral populations on surfaces, objects and bodies of water. The method includes applying thereto an effective amount of a complex of the formula

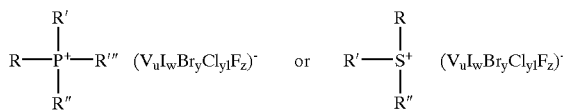

wherein R, R', R" and R''' are each independently a straight or branched, saturated or unsaturated, hydrocarbon group of 1 to 24 carbon atoms, in which hydrocarbon is unsubstituted or substituted by carboxyl, or alkylamido, or in which the hydrocarbon chain is uninterrupted or interrupted by a heteroatom; an aryl group, or aralkyl group in which alkyl has 1 to 4 carbon atoms;

V is a non-halogen anion;

u is an integer from 0 to 6;

w is an integer from 1 to 8;

y and $y_1$ are each independently integers from 0 to 4; and z is an integer from 0 to 1.

The invention is also found in a process for preparing a solvent-free liquid, gel, powder, or solid antimicrobial or antiviral complex, the process including steps of applying or generating heat to a mixture of a solid, gel, or powder composition having a source of a protonizable phosphorus or sulfur compound and a halide source. The process further includes cooling the resulting complex to ambient temperature.

DETAILED DESCRIPTION OF THE INVENTION

The invention involves a complex for antimicrobial or antiviral use, including the product of the in-situ, i.e., in place, reaction of a source of a protonizable phosphorous or sulfur compound and a halide or halogen source, e.g., a metal or ammonium halide salt; wherein the reaction is preferably conducted in an aqueous, non-aqueous, gel, aerosol, solid phase or powdered media. Preferably, for each part by weight of the halide source there is about 1 to 30 parts by weight of the phosphorous or sulfur compound, and, if desired, about 0.1 to 40 parts by weight of an oxidant, preferably a peroxygen compound. In an aqueous reacted solution, or in a use solution, the pH is about 9.5 or less.

The complex of the invention may be prepared from the in-situ reaction being carried out in water, a non-aqueous liquid, a gel, or aerosol. Alternately, another process lies in the in-situ reaction in a powder or solid state with water vapor or hydrating compounds present; while yet another process may be carried out with an oxidizing gas passing into the powder or solid or a non-aqueous liquid.

Preferably, the phosphorous or sulfur source is of the formula

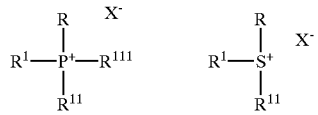

wherein X is an anion, and R, $R^1$, $R^{11}$ and $R^{111}$ are each independently a straight or branched, unsaturated or saturated, hydrocarbon group of 1 to 24 carbon atoms, in which the hydrocarbon chain is unsubstituted or substituted by carboxyl, or alkylamido, or in which the hydrocarbon chain is uninterrupted or interrupted by a heteroatom; an aryl group, or aralkyl group in which alkyl has 1 to 4 carbon atoms. One embodiment of the formula includes a compound where $R^1$ is benzyl and $R^{11}$ is aryl or benzyl. Examples of suitable protonizable phosphorus compounds include hexadecyl tributyl phosphonium or hexabutyl phosphonium salts. An example of a suitable protonizable sulfur compound is a trimethyl sulfonium salt.

An alkyl group is defined as a paraffinic hydrocarbon group which is derived from an alkane by removing one hydrogen from the formula. The hydrocarbon group may be linear or branched. Simple examples include methyl ($CH_3$) and ethyl ($C_2H_5$). However, in the present invention, at least one alkyl group may be medium or long chain having, for example, 8 to 16 carbon atoms, preferably 12 to 16 carbon atoms.

An alkylamido group is defined as an alkyl group containing an amide functional group: —$CONH_2$, —CONHR, —CONRR'.

A heteroatom is defined as a non-carbon atom which interrupts a carbon chain. Typical heteroatoms include nitrogen, oxygen, phosphorus, and sulfur.

An aryl group is defined as a phenyl, benzyl, or naphthyl group containing 6 to 14 carbon atoms and in which the aromatic ring on the phenyl, benzyl or naphthyl group may be substituted with a $C_1$–$C_3$ alkyl. An aralkyl group is aryl having an alkyl group of 1 to 4 carbon atoms.

An anion is defined as that which, when combined with the protonizable phosphonium or sulfonium cation, forms a salt. Examples of suitable anions include, for example, chloride, bromide or iodide ions, acetate, sulfate and methyl ethyl sulfate.

Oxidants

In addition to the source of protonizable phosphorous or sulfur, an oxidizing agent can be included. It is possible to utilize oxidants such as hypochlorites, chlorates, chlorites, permanganates, nitrates, or nitric acid, etc.; or gaseous oxidants such as ozone, oxygen, chlorine dioxide, chlorine, sulfur dioxide, etc. Preferred compounds include peroxides and various percarboxylic acids, including percarbonates, perborates, and persulfates. The preferred peroxygen compound is hydrogen peroxide, peracetic acid, or a percarbonate. The percarbonate can be formed in situ as a mixture of hydrogen peroxide and sodium bicarbonate. Percarboxylic acids may also be formed in situ by use of a combination of hydrogen peroxide and the desired carboxylic acid. For solid compositions, the use of percarbonates, perborates, persulfates, etc., are useful; especially where the backbone substrate (e.g., carbonate) itself is not essentially oxidized but instead acts as a substrate for the peroxygen complex. Most preferred is sodium percarbonate in solid formulations; however, gaseous oxidants are useful for non carbonate containing compositions. For liquid compositions, hydrogen peroxide or peracetic acid are the preferred oxidants; however, hypochlorites, chlorites, or ozone might also be employed for in-situ preparations. Ultimately, any oxidant that can convert the halide source into its complexed form is acceptable.

Halides

There are a large number of possible halide sources useful in the present invention such as metal or ammonium halides, haloforms or other organic halogens, or elemental halogens. Preferred metal halides include alkali metal iodide salts of the formula $MI_n$, and $MBr_n$ wherein M is a metal ionic species and n is a number equal to the metal valence. Preferred alkali metals are sodium and potassium. Other preferred halides include bromides and chlorides. A preferred embodiment uses a metal halide salt which includes a mixture of halide salts containing at least one iodide salt. The alkali metal is preferably sodium or potassium. Another preferred embodiment uses a single metal halide salt which is an iodide or bromide salt. A preferred salt is potassium iodide, cuprous iodide or a mixture thereof. Also useful are sources containing halides such as sea water, kelp, table salt, etc.

Acids

The invention can also include, if necessary, an acid component for controlling the use solution pH. Mineral and organic acids are useful for pH adjustment. The acid source might, for example, be an inorganic-based acid such as phosphoric, sulfuric, hydrochloric, nitric, sulfamic; or organic-based such as malic acid, tartaric acid, citric acid, acetic acid, glycolic, glutamic acid, sorbic acid, benzoic acid, succinic acid, or dimer and fatty acids; or mixtures thereof. Alternatively, the source of acidity can include an acid salt such as sodium diacetate, monobasic potassium or sodium phosphate. Additionally, carbonation acidification via the interaction of carbon dioxide with water is possible for aqueous formulations.

Wetting Agents

The compositions described herein can includes standard nonionic, anionic, cationic, or amphoteric compounds for surface tension reduction, wetting, and detersiveness. For example, linoleic acid, alkyl glycosides, alcohol ethoxylates, nonylphenol ethoxylates, alkanolamides, alkylbenzene sulfonates, petroleum sulfonates, diphenylether sulfonates, alpha-olefin sulfonates, stearyl citrate, alkyl naphthalene sulfonates, Pluronics® and various short-chain fatty acids are all readily useful. The wetting agents are typically not necessary for affecting the microbial reduction, but are present for detersive and surface tension reduction reasons; however, some may be employed as part of the synergistic, in-situ, antimicrobial formula.

Likewise, inerts might be added as fillers, buffers, chelants, anticaking agents, etc. For example, formulations have been prepared with: sodium chloride, bicarbonates, sulfates, silicates, phosphates, cellulosic derivatives, and EDTA.

Film Forming Agents

The composition of the invention may also contain one or more rheology modifiers, to enhance viscosity, or thicken and cause the aqueous treatment to cling to the surface being treated. Clinging enables the composition to remain in contact with the transient and resident pathogenic bacteria for longer periods of time, thereby promoting microbiological efficacy and resisting waste because of excessive dripping. The rheology modifier may be a film former or may act cooperatively with a film forming agent to form a barrier that provides additional protection.

Preferred rheology modifiers include colloidal aluminum silicate, colloidal clays, polyvinyl pyrrolidone, polyvinyl acetate, polyvinyl alcohol, polyalkylene oxides, polyacrylamides, or mixtures thereof.

Water soluble or water dispersible rheology modifiers that are useful can be classified as inorganic or organic. The organic thickeners can further be divided into natural synthetic polymers with the latter still further subdivided into synthetic natural-based synthetic petroleum-based.

Organic thickeners are generally compounds such as colloidal magnesium aluminum silicate (Veegum), colloidal clays (Bentonites), or silicas (Cab-O-Sils) which have been fumed to create particles with large surface size ratios.

Natural hydrogel thickeners of use are primarily vegetable derived exudates. For example, tragacanth, karaya, and acacia gums; and extractives such as caragheenan, locust bean gum, guar gum and pectin; or, pure culture fermentation products such as xanthan gum are all potentially useful in the invention. Chemically, all of these materials are slats of complex anionic polysaccharides. Synthetic natural-based thickeners having application are cellulosic derivatives wherein the free hydroxyl groups on the linear anhydro-glucose polymers have etherified or esterified to give a family of substances which dissolve in water and give viscous solutions. This group of materials includes the alkyl and hydroxyalkylcelluloses, specifically methylcellulose, hydroxyethylmethylcellulose, hydroxypropylmethylcellulose, hydroxybutylmethycellulose, hydroxyethylcellulose, ethylhydroxyethylcellulose, hydroxypropylcellulose, and carboxymethylcellulose. Synthetic petroleum-based water soluble polymers are prepared by direct polymerization of suitable monomers of which polyvinylpyrrolidone, polyvinylmethylether, polyacrylic acid and polymethacrylic acid, polyacrylamide, polyethylene oxide, and polyethyleneimine are representative.

All thickeners do not work with equal effectiveness in this invention. Preferred aqueous thickening agents are those which are extremely pseudoplastic (non-Newtonian, rapid relaxation), tend not to develop rigid three-dimensional structure from interpolymer interactions, have a low or negligible viscoelastic character and possess a high gel strength. Such rheological properties are manifested in a composition which has a smooth flowing appearance, is easy to pour and apply, coats uniformly without forming mucilage streamers as the applicator is withdrawn and remains firmly in place without significant sag. Examples of preferred rheology modifiers are xanthan gum and hydroxyalkylcelluloses.

Generally, the concentration of thickener used in the present invention will be dictated by the method of application. Spraying or misting requires a lower composition viscosity for easy and effective application of treatment than dipping. Film forming barrier dips typically require high apparent viscosity necessary to form thick coatings which insure improved prophylactic effect.

Additional film forming agents are included which typically work in conjunction with thickeners. In fact, many of the aforementioned rheology modifiers are themselves film formers of greater or lesser effectiveness; however, a preferred grade of polyvinyl alcohol when used with preferred thickeners such as xanthan gum or hydroxyalkylcelluloses affords particularly useful properties to compositions of this teaching, most notably the development of "balanced" films which are sufficiently water-sensitive to be stripped off with conventional washing, but capably adherent to withstand premature loss of integrity between applications. The success of the barriers thus formed by compositions of this invention are, in part, a consequence of a hydrophobic-hydrophilic balance, caused when non-volatile ingredients, especially fatty acids, surfactants and hydrotropes, become resident throughout the film and whose individual properties become additive with those characteristics of the thickeners and film formers. Such inclusions also plasticize the film and render it pliable.

Polyvinyl alcohol is a polyhydroxide polymer having a polymethylene backbone with pendent hydroxy groups. The monomer does not exist, so the polyvinyl alcohol moiety is made by first forming polyvinyl acetate and removing acetate groups using a base catalyzed methanolysis. Polyvinyl acetate polymerization is accomplished by conventional processes and the degree of hydrolysis is controlled by preventing completion of the methanol reaction. Variation of film flexibility, water sensitivity, ease of salvation, viscosity, film strength and adhesion can be varied by adjusting molecular weight and degree of hydrolysis. The preferred polyvinyl alcohol for use in compositions herein has a degree of hydrolysis greater than 92%, preferably greater than 98%, most preferably greater than 98.5%; and, has a molecular weight that falls in the range of between about 15,000 and 100,000, but preferably between 40,000 and 70,000 corresponding to a solution viscosity (4% wt aqueous solution measured in centipoise (cP) at 20° C. by Hoeppler falling ball method) of 12–55 cP (0.012 to 0.055 Pa·s) and 12–25 cP (0.012 to 0.025 Pa·s) respectively.

Use

It is believed that the working compound in the composition of the invention is a poly-halogen salt of the phosphonium or sulfonium cation. The poly-halogen salt can include an anion of the formula $I_w Br_y Cl_{y_1} F_z$, wherein w is an integer from 1 to 8, y and $y_1$ are each independently integers from 0 to 4, and z is an integer from 0 to 1. In a typical reaction, for example, a protonizable phosphorous or sulfur compound reacts with potassium iodide to produce the poly-halogen salt. In a preferred embodiment, an oxiding agent is also present. If only KI is used, the poly-halogen anion is represented by $I_w$, where w ranges from 1 to 8. If KBr is also added to the reaction mixture, the resulting interhalogen anion is represented by $I_w Br_y$, where w plus y equals 2 to 9. If a quaternary ammonium chloride is used the reaction with potassium iodide in the presence of an oxidizing agent would produce an inter-halogen salt; however, in contrast to other known interhalogens containing three or less halogen atoms the current art contains 4 or more. While an inorganic metal bromide is optional in the reaction mixture, the inorganic metal or ammonium iodide is not. The product requires the presence of at least some inorganic metal or ammonium iodide.

The aqueous solution of the invention, made by the in-situ reaction or by addition of the pre-made complex to a solution, is characterized by a yellow to red color which serves as an indicator of solution effectiveness. As long as the color remains, the solution retains good killing properties. The effective time period is about 50 hours. Generally for unbuffered or non-acidic formulations, as the reaction takes place, the pH of the solution increases from about 5 to about 10. At the same time, the oxidation/reduction potential (ORP) increases accordingly. This is noteworthy since ORP normally is in inversely proportional to pH and, thus, indicates a very active oxidizing species being formed.

According to the invention, use solutions are aqueous solutions containing a source of protonizable phosphorous or sulfur compound, a metal or ammonium halide and any resulting reaction products. It has been discovered that the preferred ratio between the two added ingredients, the protonizable phosphorous or sulfur compound, and the halide source, e.g. metal or ammonium halides, respectively can range from about 0.1 to about 30 parts by weight of the phosphorous or sulfonium compound for each part by weight of the halide source.

Use solutions are formed by combining, in an aqueous medium, the individual components consisting of a protonizable phosphorous or sulfur compound, optionally a per-oxygen compound and a metal halide. Reaction is virtually instantaneous, resulting in a use solution which can be used almost immediately. Alternately, the use solution can be formed by incorporating the pre-made complex into a solution. The use solution can be utilized in any application needing either antimicrobial or oxidizing efficacy.

The antimicrobial compositions of the invention are either solid-phase, powdered, gels, aerosols, non-aqueous liquids, or 2-part liquid mixtures which can be added to an aqueous rinse or wash liquid or a non-aqueous (e.g., mineral oil, lecithin) formulation.

By way of illustration, typical powdered formulation ranges are:

| Component | Useful Wt-% | Preferred Wt-% | More Preferred Wt-% |
|---|---|---|---|
| phosphorous or sulfur source | 0.1–30 | 1–15 | 3–10 |
| oxidant compound | 0.1–50 | 1–25 | 5–15 |
| halide source | 0.1–60 | 1–30 | 5–15 |
| acidity source | 0–80 | 0–50 | 0–30 |
| wetting agents | 0–20 | 0–10 | 0–5 |
| inerts | 0–95 | 0–60 | 0–30 |

The present invention also includes as an alternative embodiment a two part liquid concentrate where each part contains an aqueous concentrate including a phosphorous or sulfur source in part (a) and a metal halide in part (b); and optionally, inerts and wetting agents.

Typical two part liquid formulation ranges are:

| Component | Useful Wt-% | Preferred Wt-% | More Preferred Wt-% |
|---|---|---|---|
| first part | | | |
| phosphorous or sulfur source | 0.1–80 | 0.5–50 | 1–15 |
| oxidant compound | 0.1–75 | 1–35 | 10–20 |
| acidity source | 0–70 | 0–50 | 0–25 |
| wetting agents | 0–10 | 0.05–5 | 0.1–1 |
| inerts | 0–50 | 0–20 | 0–10 |
| water | balance | balance | balance |
| second part | | | |
| halide source | 0.1–80 | 0.5–30 | 1–15 |
| wetting agents | 0–10 | 0.05–5 | 0.1–1 |
| inerts | 0–50 | 0–20 | 0–10 |
| water | balance | balance | balance |

When used, a total actives concentration ranging from 10 to 130,000 ppm is preferred. Useful product use concentration ranges for sanitizing with either a liquid or solid composition are given in the table below:

| Component | Useful (ppm) | Preferred (ppm) | More Preferred (ppm) |
|---|---|---|---|
| phosphorous or sulfur source | 1–10,000 | 10–5,000 | 20–1,000 |
| oxidant compound | 1–30,000 | 30–15,000 | 50–1,500 |
| acidity source | 0–20,000 | 0–5,000 | 0–1,000 |
| halide source | 1–30,000 | 10–15,000 | 20–1,500 |
| wetting agents | 0–5,000 | 0–500 | 0–100 |
| inerts | 0–50,000 | 0–10,000 | 0–1,000 |

The invention includes a process for preparing a solvent-free liquid, gel, aerosol, powder, or solid antimicrobial or antiviral complex including applying or generating heat, gaseous water vapor, or chemical hydrates, to a mixture of a solid, gel, or powder composition having a source of a protonizable phosphorous or sulfur compound; an oxidant; a halide source; and cooling the resulting complex to ambient temperature. In one embodiment, the mixture is heated in an extruder or hot-melt apparatus. Optionally, heat is applied or generated to a temperature above 30° C.

The invention also includes a process for making powder antimicrobial or antiviral compositions suitable for incorporation (casting, absorbing, adsorbing, spray-drying, etc.,) into solid, elastomeric, or fibrous substrates for residual antimicrobial or antiviral effects.

The complex described herein can also be used to reduce odors and microbial or viral populations in gaseous streams, bleaching of or reducing microbial or viral populations on woven or non-woven substrates.

Additionally, the compositions containing the complex are effective by themselves, or mixed with other adjuvants, in reducing microbial and viral populations in applications in the food industry. These include food preparation equipment, belt sprays for food transport lines, boot and hand-wash dip-pans, food storage facilities and anti-spoilage air circulation systems, aseptic packaging sanitizing, food refrigeration and cooler cleaners and sanitizers, warewashing sanitizing, blancher cleaning and sanitizing, food packaging materials, cutting board additives, third-sink sanitizing, beverage chillers and warmers, meat chilling or scalding waters, sanitizing gels, food processing antimicrobial garment sprays, and non-to-low-aqueous food preparation lubricants, oils, and rinse additives.

The invention further includes a process for preparing antimicrobial and antiviral compositions suitable for subsequent incorporation into solid, gel, aerosol, or non-aqueous liquid cleaning, sanitizing, or disinfecting products for treatment of surfaces. Thus, these include in powder, liquid, gel, or solid form: a) a source, preferably a natural one, of a protonizable phosphorous or sulfur compound; (b) a halide or halogen source; optionally (c) an oxidant, preferably a peroxygen compound or oxidizing gas; and optionally (d) a source of acidity; wherein for each part by weight of the halide source there is about 0.1 to 30 parts by weight of the phosphorous or sulfur compound, and if desired, about 0.1 to 40 parts by weight of the oxidant compound, unless an oxidizing gas is use to form the complex in-situ and, then, an excess of the oxidant can be employed. The antimicrobial or antiviral composition is incorporated into the cleaning, disinfecting, or sanitizing substrate at a level of about 0.001 to about 95 weight %.

The invention includes a number of antimicrobial and antiviral methods and processes. The invention can be found in a method of reducing microbial or viral populations on a surface or object; said method including treating said surface or object with an aqueous solution of an effective amount of a complex resulting from an in-situ reaction of a source of a protonizable phosphorous or sulfur compound, an oxidant, and a halide source. In one embodiment, the surface is a clean-in-place (CIP) system, while in another it is one of the many non-CIP surfaces encountered in preparing food (e.g., cutting boards, sinks, ware-wash systems, utensils, counter tops, transport belts, aseptic packaging, boot and hand-wash dip-pans, food storage facilities and anti-spoilage air circulation systems, food refrigeration and coolers, blanchers, food packaging materials, third-sink containers, etc.).

These surfaces can be those typified as "hard surfaces" (such as walls, floors, bedpans, etc.,), or woven and non-woven surfaces (such as surgical garments, draperies, bed linens, bandages, etc.,), or patient-care equipment (such as respirators, diagnostic equipment, shunts, body scopes, etc.,), or a plethora of surgical and diagnostic equipment. Also, the medical-related surfaces might be those of medical waste or blood spills.

The invention also includes a method of reducing microbial or viral populations in a body or stream of water including treating said body or stream with an effective amount of a complex resulting from an in-situ reaction of a source of a protonizable phosphorous or sulfur compound, an oxidant, and a halide source. The body of water can be a swimming pool or a cooling tower, or can alternatively include food processing waters (e.g., flumes, can warmers, retort waters, third-sink sanitizing, bottle coolers, food sprays and misting systems, etc.,). beverage chillers and warmers, meat chilling or scalding waters, sanitizing gels, food processing antimicrobial garment sprays, and non-to-low-aqueous food preparation lubricants, oils, and rinse additives.

The complex resulting from an in-situ reaction of a source of a protonizable phosphorous or sulfur compound and a halide source can also be used to reduce odors and microbial or viral populations in gaseous (especially air) streams by passing said aqueous streams through a bed, or woven or non-woven substrate or filter, including said complex. The complex can also be used for bleaching or reducing microbial or viral populations on woven or non-woven substrates, like linens or garments, by treating said substrate with an aqueous solution including the complex.

Treatment of inanimate objects can be accomplished by spraying or wiping a use solution onto the object or surface. An object can also be treated via submersion into an adequate supply of the use solution, which is typically an aqueous solution containing a major proportion of water and an effective amount of an antimicrobial or antiviral complex. The use solution can also contain one or more film forming agents to prevent excessively rapid shedding of the treatment solution. Volumes of water, such as those found in swimming pools, water cooling towers and food process and transport streams, can be treated by addition of the complex (either made in-situ or pre-made via non-aqueous routes) to a concentrated liquid, gel, aerosol, solid, or powder to the water. Addition can take place within the main volume of water, or can occur within a makeup stream of fresh water being added to the main volume. Non-aqueous medium (such as oils or plastics) can be treated using an in-situ complex, or by incorporation of a pre-made complex.

The following examples further describe the present invention by way of illustration and are not meant to be limiting thereon.

WORKING EXAMPLE 1

It has been discovered that particular attributes can be used as evidence of in situ formation of the antimicrobial and antiviral compositions described herein. One suitable attribute is the UV-visible (UV-vis) absorption spectrum. Table 1 below describes the UV-vis results for several combinations of phosphonium and sulfonium polyhalide salts in comparison with several quaternary ammonium polyhalide slats and molecular iodine. In the Table, lines 7–12 represent the phosphonium and sulfonium salts while lines 3–6 represent the ammonium salts and lines 1–2 represent molecular iodine.

Sample Preparations

Tetradecyl tributyl phosphonium chloro diiodide (line 7 in Table 1) was prepared by combining 5.0 g (0.0197 moles) of $I_2$ with 8.8 g (0.0202 moles) of tetradecyl tributyl phosphonium chloride to form a dark brown liquid. A temperature of 120° F. was used to increase reaction speed. 4 g of the resultant complex was combined with 96.0 g of citric acid to form a moist brown powder that clings to plastic.

Similarly, trimethyl sulfonium triuodide (line 12 in Table 1) was prepared by combining 5.0 (0.019 moles) g of $I_2$ with 3.95 g (0.019 moles) of trimethyl sulfonium iodide to form a black liquid that does not readily wet plastic. 4.0 g of the resultant complex was combined with 96.0 g of citric acid to form a brown powder that turns yellow/green in water.

As seen, the phosphonium and sulfoniun salts have a UV-vis absorbance at about 355 to 375 nm, in stark contrast to the free iodide absorbance at about 285 to 305 nm or 460 nm. The phosphonium and sulfonium salts have a UV-vis absorbance essentially equivalent to that demonstrated by the quaternary ammonium salts tested. As described hereinafter, these phosphonium and sulfonium compositions have strong antimicrobial activity similar in capacity to the nitrogen-based analogues.

TABLE 1

| Composition | Preparation Method | Distinguishing UV-vis Maximum |
|---|---|---|
| Iodine | | |
| 1 iodine in pH = 3 water | molecular $I_2$ | 285–305 nm, 460 nm |
| 2 iodine in pH = 3 water | in-situ using $KI/H_2O_2$[1] | 285–305 nm, 460 nm |
| Quaternary Ammonium | | |
| 3 didecyl dimethyl ammonium chloro diiodide | pre-made salt[2] | 355–375 nm |
| 4 choline chloro diiodide | pre-made salt[3] | 355–375 nm |
| 5 didecyl dimethyl ammonium chloro diiodide | in-situ using $KI/H_2O_2$[4] | 355–375 nm |
| 6 choline chloro diiodide | in-situ using $KI/H_2O_2$[4] | 355–375 nm |
| Phosphonium and Sulfonium | | |
| 7 tetradecyl tributyl phosphonium chloro diiodide | pre-made salt[5] | 355–375 nm |
| 8 hexadecyl tributyl phosphonium chloro diiodide | in-situ using $KI/H_2O_2$[4] | 355–375 nm |
| 9 tetrabutyl phosphonium bromo diiodide | in-situ using $KI/H_2O_2$[6] | 355–375 nm |
| 10 tetrabutyl phosphonium bromo diiodide | pre-made salt[7] | 355–375 nm |
| 11 hexadecyl tributyl phosphonium chloro diiodide | in-situ using $KI/KBr/H_2O_2$[8] | 355–375 nm |
| 12 trimethyl sulfonium triiodide | pre-made salt[9] | 355–375 nm |

[1]Generated using a molar ratio of KI to peroxide of 2:3.
[2]Generated using a molar ratio of didecyl dimethyl ammonium chloride to $I_2$ of 1:1.
[3]Generated using a molar ratio of choline chloride to $I_2$ of 1:1.
[4]Generated using a molar ratio of quaternary heteroatom chloride component to KI to peroxide of 1:2:3.
[5]Generated using a molar ratio of hexadecyl tributyl phosphonium chloride to $I_2$ of 1:1.
[6]Generated using a molar ratio of the phosphonium bromide component to KI to peroxide of 1:2:3.
[7]Generated using a molar ratio of tetrabutyl phosphonium bromide to $I_2$ of 1:1.
[8]Generated using a molar ratio of the phosphonium chloride component to KI to KBr to peroxide of 1:1:2:4.
[9]Generated using a molar ratio of trimethyl sulfonium triiodide to $I_2$ of 1:1.

WORKING EXAMPLE 2

The data displayed in Table 2 below demonstrates the biocidal efficacy of the phosphonium and sulfonium compositions in comparison to the nitrogen-based polyhalide controls. Similar to the nitrogen-based compounds, the phosphonium and sulfonium compounds can achieve substantial microbial reductions (greater than a 3-log reduction in only 30 seconds).

TABLE 2

| Composition | Total Active (mmole/liter) | Log Reduction (S. aureus) (30 seconds) | Log Reduction (S. aureus) (60 seconds) |
|---|---|---|---|
| Nitrogen Polyhalide Controls | | | |
| 1 choline chloro diiodide | 0.32 | >6.9 | >6.9 |
| 2 tetrabutyl ammonium chloro diiodide | 0.12 | >6.4 | >6.4 |
| 3 tetramethyl ammonium chloro diiodide | 0.17 | 4.0 | >6.8 |
| Phosphonium and Sulfonium Polyhalides | | | |
| 4 trimethyl sulfonium triiodide | 0.28 | >7.0 | >7.0 |
| tributyl hexadecyl phosphonium chloro diiodide | 0.89 | 5.0 | 6.2 |

WORKING EXAMPLE 3

This Example demonstrates the antimicrobial efficacy of a phosphonium compound and a sulfonium compound as described herein. A 4% solution of trimethyl sulfonium triiodide and a solution of 20% hexadecyl tributyl phosphonium diiodochloride were tested at a concentration of 12 grams per gallon in sterile deionized water against *Staphylococcus aureus* (ATCC 6538). As seen below in Table 3, the sulfonium compound tested achieved a >5 log reduction after 30 seconds while the phosphonium compound tested achieved a similar log reduction after 5 minutes.

TABLE 3

| Test Substance | Exposure Time | Log Reduction | pH |
|---|---|---|---|
| 4% trimethyl sulfonium triiodide | 15 seconds | 4.67 | |
| | 30 seconds | >6.95 | 2.52 |
| | 5 minutes | >6.95 | |
| 20% hexadecyl tributyl phosphonium diiodochloride | 15 seconds | 3.74 | |
| | 30 seconds | 4.98 | 4.61 |
| | 5 minutes | 6.21 | |

Test Procedures:

| | |
|---|---|
| Test System: | *Staphylococcus aureus* (ATCC 6538) |
| Test Temperature: | Ambient |
| Exposure Times: | 15 seconds, 30 seconds and 5 minutes |
| Neutralizer: | 33% Chambers and 66% of 1% sodium thiosulfate |
| Plating Medium: | Tryptone Glucose Extract Agar |
| Incubation: | 37° C. for 48 hours |

The above specification, examples and data provide a complete description of the manufacture and use of the composition of the invention. Since many embodiments of the invention can be made without departing from the spirit and scope of the invention, the invention resides in the claims hereinafter appended.

We claim:

1. A composition for antimicrobial or antiviral use, comprising the product of an in-situ reaction of:

(a) a source of a protonizable phosphorus compound of the formula:

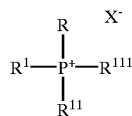

wherein X is an anion, R, $R^1$, $R^{11}$ and $R^{111}$ are each independently a straight or branched, saturated or unsaturated hydrocarbon group of 1 to 24 carbon atoms, in which the hydrocarbon is unsubstituted or substituted by carboxyl, or alkylamido, or in which the hydrocarbon chain is uninterrupted or interrupted by a heteroatom; an aryl group, or aralkyl group in which alkyl has 1 to 4 carbon atoms; and (b) a halide source containing at least two moles of iodide for every one mole of chloride or bromide.

2. The composition of claim 1 which further comprises an oxidant.

3. The composition of claim 1, wherein the reaction in an aqueous medium is at a pH of less than about 9.5.

4. The composition of claim 1, wherein the protonizable phosphorus compound is a hexadecyl tributyl phosphonium or a hexabutyl phosphonium salt.

5. The composition of claim 2, wherein the oxidant is hydrogen peroxide.

6. The composition of claim 2, wherein the oxidant comprises a percarboxylic acid.

7. The composition of claim 2, wherein the oxidant comprises a percarbonate, a perborate, a persulfate, or mixtures thereof.

8. The composition of claim 2, wherein the oxidant is a chlorite, hypochlorite, nitrate salt, or a mixture thereof.

9. The composition of claim 2, wherein the oxidant is a gas selected from the group consisting of ozone, sulfur dioxide, oxygen, chlorine, and chlorine dioxide.

10. The composition of claim 1, wherein the composition further comprises inerts, acidulants, and surfactants.

11. The composition of claim 2, wherein the composition further comprises inerts, acidulants, and surfactants.

12. The composition of claim 1, wherein the composition in aqueous solution has an ultraviolet absorption maximum at about 355–375 nm.

13. The composition of claim 2, wherein the composition in aqueous solution has an ultraviolet absorption maximum at about 355–375 nm.

14. A process for the preparation of a non-aqueous liquid, gel, solid, elastomeric or fibrous antimicrobial or antiviral composition comprising: incorporating the composition of claim 1 into a non-aqueous liquid, gel, solid, elastomeric or fibrous substrate, wherein the substrate has a water solubility of greater than 0.1 wt-% at 25° C.

15. A method of reducing microbial or viral populations on a surface or object; said method comprising treating said surface or object with an aqueous or non-aqueous solution or gel of an effective amount of a composition according to claim 1.

16. The method of claim 15, wherein the dilute aqueous or non-aqueous solution comprises about 0.1 to 600 grams per liter of said composition.

17. The method of claim 15, wherein the surface is a clean-in-place system, a clean-out-of-place system, a warewash machine, or a sink.

18. A method of reducing microbial or viral populations in a body or stream of water comprising treating said body or stream with an effective amount of a composition of claim 1.

19. The method of claim 18, wherein the body of water is a swimming pool.

20. The method of claim 18, wherein the body of water is a cooling tower.

21. A method of reducing odors and microbial or viral populations in gaseous streams comprising passing said aqueous streams through a bed comprising a composition of claim 1.

22. A method of bleaching of or reducing microbial or viral populations on woven or non-woven substrates; said method comprising treating said substrate with an aqueous solution comprising a composition according to claim 1.

23. An antimicrobial or antiviral composition comprising a combination of:

(a) a source of a protonizable phosphorus compound of the formula:

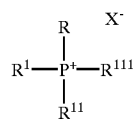

wherein X is an anion, R, $R^1$, $R^{11}$ and $R^{111}$ are each independently a straight or branched, saturated or unsaturated hydrocarbon group of 1 to 24 carbon atoms, in which the hydrocarbon is unsubstituted or substituted by carboxyl, or alkylamido, or in which the hydrocarbon chain is uninterrupted or interrupted by a heteroatom; an aryl group, or aralkyl group in which alkyl has 1 to 4 carbon atoms;

(b) a halide source containing at least two moles of iodide for every one mole of chloride or bromide; and (c) the balance being water.

24. The composition of claim 23, wherein the composition has a pH of less than about 9.5.

25. The composition of claim 23, wherein the protonizable phosphorus compound is a hexadecyl tributyl phosphonium or a hexabutyl phosphonium salt.

26. The composition of claim 23, which further comprises an oxidant.

27. The composition of claim 26, wherein the oxidant is hydrogen peroxide.

28. The composition of claim 26, wherein the oxidant comprises a percarboxylic acid.

29. The composition of claim 26, wherein the oxidant comprises a percarbonate, a perborate, a persulfate, or mixtures thereof.

30. The composition of claim 26, wherein the oxidant is a chlorite, hypochlorite, nitrate salt, or a mixture thereof.

31. The composition of claim 26, wherein the oxidant is a gas selected from the group consisting of ozone, sulfur dioxide, oxygen, chlorine, or chlorine dioxide.

32. The composition of claim 23, wherein the composition further comprises inerts, acidulants, and surfactants.

33. The composition of claim 26, wherein the composition further comprises inerts, acidulants, and surfactants.

34. The composition of claim 23, wherein the composition in aqueous solution has an ultraviolet absorption maximum at about 355–375 nm.

35. The composition of claim 26, wherein the composition in aqueous solution has an ultraviolet absorption maximum at about 355–375 nm.

36. A two-part liquid concentrate antimicrobial and antiviral composition comprising:

in one part:
(a) about 0.1 to 80 wt-% of a source of a protonizable phosphorus compound of the formula:

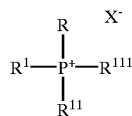

wherein X is an anion, R, $R^1$, $R^{11}$ and $R^{111}$ are each independently a straight or branched, saturated or unsaturated hydrocarbon group of 1 to 24 carbon atoms, in which the hydrocarbon is unsubstituted or substituted by carboxyl, or alkylamido, or in which the hydrocarbon chain is uninterrupted or interrupted by a heteroatom; an aryl group, or aralkyl group in which alkyl has 1 to 4 carbon atoms;

(b) the balance being water; and in the second part:

(c) about 0.1 to 80 wt-% of a halide source containing at least two moles of iodide for every one mole of chloride or bromide; and (d) the balance being water.

37. The composition of claim 36, wherein the first part further comprises an oxidant.

38. The composition of claim 36, wherein each part further comprises, independently, inerts, builders, chelants, and surfactants.

39. A method of reducing the microbial or viral count on a surface or object comprising:

(a) mixing the two part liquid concentrate according to claim 36 in water to provide a dilute aqueous solution of about 0.1 to 130,000 ppm of the total concentrate; and (b) treating said surface or object with the resulting dilute aqueous solution.

40. The method of claim 39, wherein the surface is a clean-in-place system, a clean-out-of-place system, a warewash machine, or a sink.

41. A method of reducing microbial or viral populations on surfaces, objects and bodies of water comprising applying thereto an effective amount of a complex of the formula

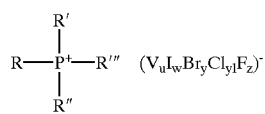

wherein R, R', R" and R'" are each independently a straight or branched, saturated or unsaturated, hydrocarbon group of 1 to 24 carbon atoms, in which hydrocarbon is unsubstituted or substituted by carboxyl, or alkylamido, or in which the hydrocarbon chain is uninterrupted or interrupted by a heteroatom; an aryl group, or aralkyl group in which alkyl has 1 to 4 carbon atoms;

V is a non-halogen anion;

u is an integer from 0 to 6;

w is an integer from 1 to 8;

y and $y_1$ are each independently integers from 0 to 4; and z is an integer from 0 to 1, wherein the sum of w, y and $y_1$ is at least 2.

42. The method of claim 41, wherein the complex is hexadecyl tributyl phosphonium chlorodiiodide.

43. The method of claim 41, wherein the complex is tetrabutyl phosphonium bromodiiodide.

44. The method of claim 41, wherein the complex is hexadecyl tributyl phosphonium chlorobromodiiodide.

45. An antimicrobial and antiviral film comprising an effective amount of a complex of the formula

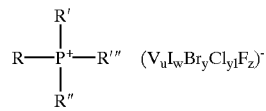

wherein R, R', R" and R'" are each independently a straight or branched, saturated or unsaturated, hydrocarbon group of 1 to 24 carbon atoms, in which hydrocarbon is unsubstituted or substituted by carboxyl, or alkylamido, or in which the hydrocarbon chain is uninterrupted or interrupted by a heteroatom; an aryl group, or aralkyl group in which alkyl has 1 to 4 carbon atoms;

V is a non-halogen anion;

u is an integer from 0 to 6;

w is an integer from 1 to 8;

y and $y_1$ are each independently integers from 0 to 4; and z is an integer from 0 to 1, wherein the sum of w, y and $y_1$ is at least 2;

and one or more rheology modifiers.

46. The film of claim 45, wherein the rheology modifier is an inorganic or organic thickener, or a mixture thereof.

47. The film of claim 46, wherein the thickener is a natural or synthetic polymer.

48. The film of claim 45, wherein the rheology modifier comprises colloidal aluminum silicate, colloidal clays, polyvinyl pyrrolidone, polyvinyl acetate, polyvinyl alcohol, polyalkylene oxides, polyacrylamides, or mixtures thereof.

49. A method of reducing the microbial or viral populations on animal surfaces comprising applying to said surfaces a film according to claim 45.

50. The method of claim 49, wherein the film is applied to the surface of the animal by diluting the film with water.

51. A process for preparing a solvent-free liquid, gel, powder, or solid antimicrobial or antiviral complex comprising applying or generating heat to a mixture of a solid, gel, or powder composition comprising:

(a) a source of a protonizable phosphorus compound of the formula:

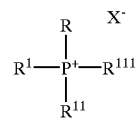

wherein X is an anion, R, $R^1$, $R^{11}$ and $R^{111}$ are each independently a straight or branched, saturated or unsaturated hydrocarbon group of 1 to 24 carbon atoms, in which the hydrocarbon is unsubstituted or substituted by carboxyl, or alkylamido, or in which the hydrocarbon chain is uninterrupted or interrupted by a heteroatom; an aryl group, or aralkyl group in which alkyl has 1 to 4 carbon atoms; and (b) a halide source containing at least two moles of iodide for every one mole of chloride or bromide; and cooling the resulting complex to ambient temperature.

52. The process of claim 51, wherein heat is applied to the composition which further comprises an oxidant.

53. The process of claim 51, wherein the mixture is heated in an extruder or hot-melt apparatus.

54. The process of claim 51, wherein heat is applied or generated to a temperature above 30° C.

55. The process of claim 51, wherein heat is generated by the application of moisture vapors or chemical hydrates.

56. An antimicrobial or antiviral composition comprising an effective amount of a complex of the formula

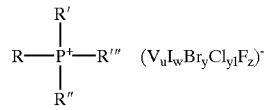

wherein R, R', R" and R'" are each independently a straight or branched, saturated or unsaturated, hydrocarbon group of 1 to 24 carbon atoms, in which hydrocarbon is unsubstituted or substituted by carboxyl, or alkylamido, or in which the hydrocarbon chain is uninterrupted or interrupted by a heteroatom; an aryl group, or aralkyl group in which alkyl has 1 to 4 carbon atoms;

V is a non-halogen anion;

u is an integer from 0 to 6;

w is an integer from 1 to 8;

y and $y_1$ are each independently integers from 0 to 4; and z is an integer from 0 to 1, wherein the sum of w, y and $y_1$ is at least 2.

57. The composition of claim 56, wherein the complex is hexadecyl tributylphosphonium chlorodiiodide.

58. The composition of claim 56, wherein the complex is tetrabutyl phosphonium bromodiiodide.

59. The composition of claim 56, wherein the complex is hexadecyl tributylphosphonium chlorobromodiiodide.

* * * * *